(12) United States Patent
Becker et al.

(10) Patent No.: US 7,347,830 B2
(45) Date of Patent: Mar. 25, 2008

(54) ASSEMBLIES AND METHODS FOR MEASURING TOOTH APEX LOCATION

(75) Inventors: Arie Becker, Kibbutz Afikim (IL); Gabriel Savin, Rishon LeZion (IL); Nachman Berger, Ramat Gan (IL); Shai Gal, Jordan Valley (IL)

(73) Assignee: Medic.NRG Ltd., Kibbutz Afikim (IL)

( * ) Notice: Subject to any disclaimer, the term of this patent is extended or adjusted under 35 U.S.C. 154(b) by 185 days.

(21) Appl. No.: 11/056,723

(22) Filed: Feb. 11, 2005

(65) Prior Publication Data

US 2005/0177074 A1 Aug. 11, 2005

(30) Foreign Application Priority Data

Feb. 11, 2004 (IL) ........................ 160335

(51) Int. Cl.
*A61C 19/04* (2006.01)
*A61C 3/00* (2006.01)
*A61C 5/12* (2006.01)
*A61B 5/103* (2006.01)
*A61B 5/117* (2006.01)

(52) U.S. Cl. ................. 600/590; 433/75; 433/139; 433/72; 600/587; 600/589

(58) Field of Classification Search ................ 600/589, 600/590, 587, 547, 554; 433/72, 75, 138, 433/139, 102, 81; 33/514
See application file for complete search history.

(56) References Cited

U.S. PATENT DOCUMENTS

| | | | | |
|---|---|---|---|---|
| 482,618 A | * | 9/1892 | Buxbaum | ............... 433/139 |
| 544,135 A | * | 8/1895 | Strout | ............... 433/139 |
| 1,143,515 A | * | 6/1915 | Dunlop | ............... 600/237 |
| 3,916,529 A | | 11/1975 | Mousseau | |
| 4,004,345 A | * | 1/1977 | Ely | ............... 433/139 |
| 4,462,802 A | | 7/1984 | Sekiya | |
| 4,571,183 A | * | 2/1986 | Nash | ............... 433/116 |
| 4,639,221 A | * | 1/1987 | Sairenji | ............... 433/139 |
| 6,390,814 B1 | * | 5/2002 | Gardiner | ............... 433/75 |
| 6,520,773 B1 | * | 2/2003 | Weber | ............... 433/27 |
| 6,613,001 B1 | * | 9/2003 | Dworkin | ............... 600/590 |

FOREIGN PATENT DOCUMENTS

| | | |
|---|---|---|
| DE | 32 11 669 | 3/1982 |
| FR | 2590476 | 11/1985 |
| JP | 2000254149 | 9/2000 |
| WO | PCT/IL02/00556 | 7/2002 |

\* cited by examiner

*Primary Examiner*—Max Hindenburg
*Assistant Examiner*—H. Q. Nguyen
(74) *Attorney, Agent, or Firm*—Milde & Hoffberg, LLP

(57) ABSTRACT

The invention provides an assembly for measuring the penetration depth of a dental instrument into a root canal of a tooth. The assembly has a base element configured to be clampingly braced onto a tooth to be treated; an electrically conductive guiding member affixable to the base element and disposed, when assembled, above the tooth, thereby, in use, a portion of the dental instrument makes electrical contact with it. The guiding member further includes an electrical terminal connectable to an apex location measuring device. Methods for continuously measuring penetration depths of a dental instrument into a root canal of a tooth are also provided.

6 Claims, 6 Drawing Sheets

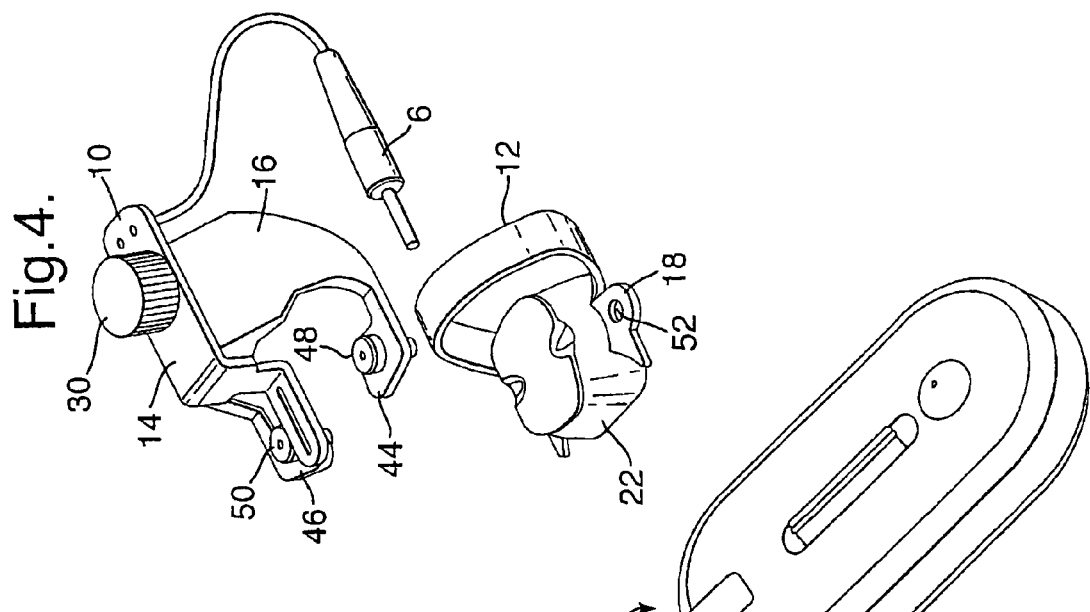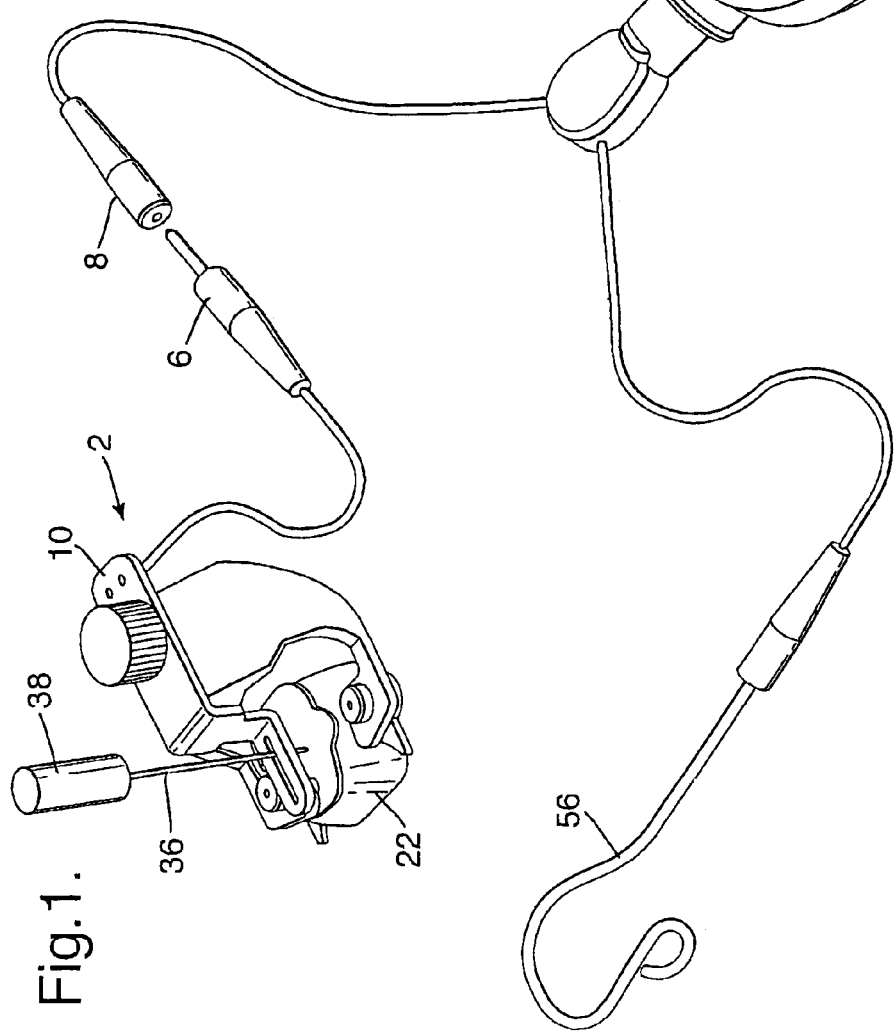

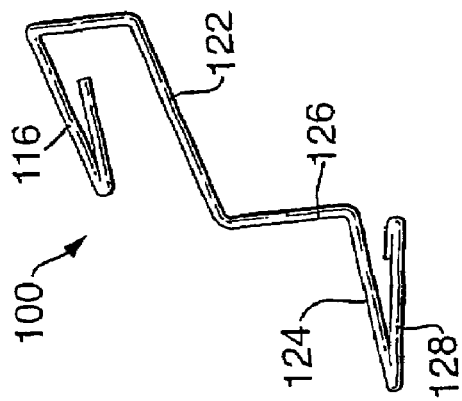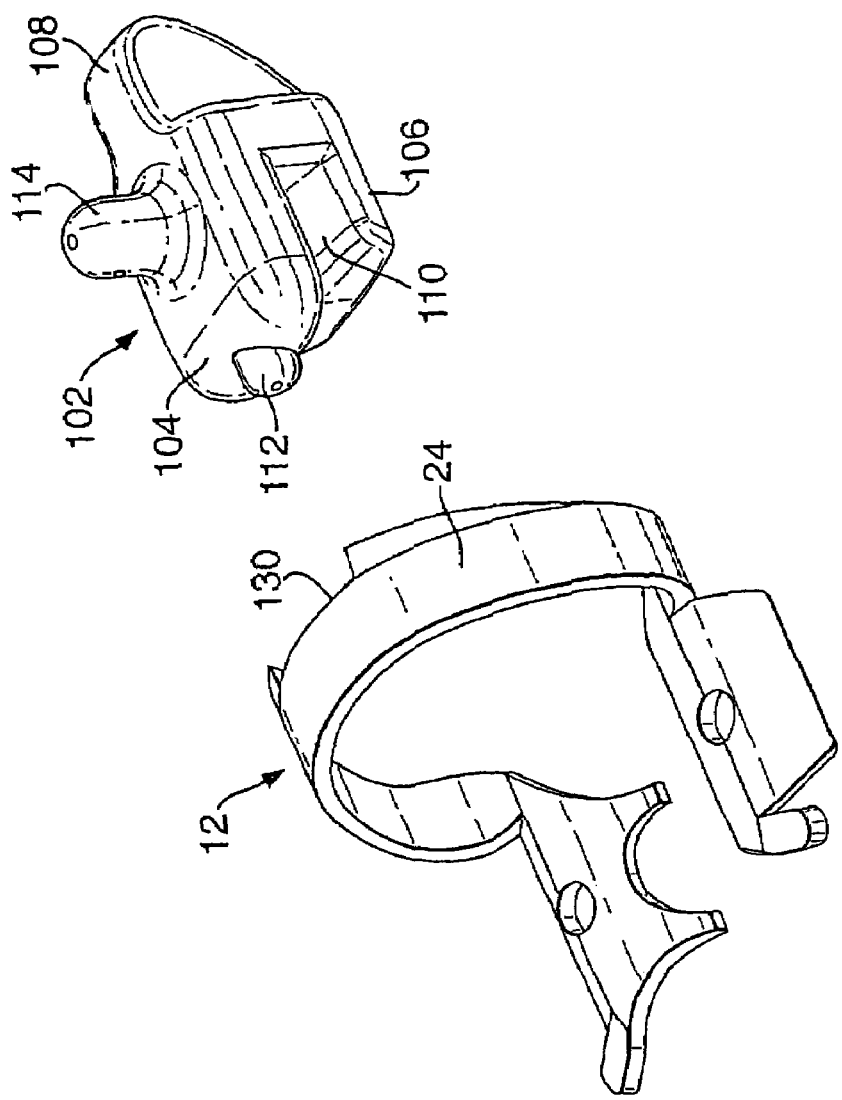
Fig.11.

ASSEMBLIES AND METHODS FOR MEASURING TOOTH APEX LOCATION

FIELD OF THE INVENTION

The present invention relates to dental instruments and more particularly to assemblies and methods for measuring and indicating penetration depth of a dental instrument into a root canal of a tooth.

BACKGROUND OF THE INVENTION

There are known in the art devices for measuring and indicating the penetration of a dental instrument into a tooth, e.g., for root canal treatments. Such devices, called apex locators, identifying the location of the biological apex, are based on relative measurement between a flexible disc-shaped depth stopper, slidingly affixed on the shaft of a dental instrument, leaning against the upper surface of the tooth to be treated, and a predetermined bore length which is believed the tooth can accommodate. It can be easily realized that the use of, and dependency on, the reference marker such as a flexible disc-shaped stopper, leaning against or touching the uneven wavy upper surface of a tooth, is less than desirable when it is necessary to attain accuracies of less than e.g., 0.5 mm. To be on the safe side, dentists take a precautionary distance of say between 0.5 mm and 1 mm from the predetermined apex, thereby leaving the edge of the root canal untreated, eventually constituting a source for development of future infection.

SUMMARY OF THE INVENTION

It is therefore a broad object of the present invention is to ameliorate the above shortcoming of the known technique of measuring the depth of a tooth root canal and to provide assemblies and methods for more accurately determining the apex location.

It is a further object of the present invention to provide assemblies and methods for accurately determining the root canal apex, while maintaining the dental instrument drilling or filing in the root canal substantially free for manual manipulation by the dentist.

In accordance with the invention, there is therefore provided an assembly for measuring the penetration depth of a dental instrument into a root canal of a tooth, comprising a base element configured to be clampingly braced onto a tooth to be treated; an electrically conductive guiding member affixable to said base element and disposed, when assembled, above said tooth, thereby, in use, a portion of said dental instrument makes electrical contact with it, and said guiding member further including an electrical terminal connectable to an apex location measuring device.

The invention further provides a method for continuously measuring penetration depth of a dental instrument into a root canal of a tooth, comprising clamping an electrically conductive guiding member above a tooth; connecting an apex location measuring device to said guiding member, and making contact between a dental instrument having a pin-shaped electrically conductive portion and the electrical conductive guiding member.

The invention still further provides a method for continuously measuring penetration depths of a dental instrument into a root canal of a tooth, comprising clamping a base element on a tooth to be treated; providing a conductive guiding member; at least indirectly affixing said conductive guiding member on the base element, above and in alignment with, said tooth; connecting a device for measuring penetration depth of a dental instrument into a tooth; providing a dental instrument having a pin-shaped electrical conductive portion, and making contact between said pin and guiding member, whereby upon a point along said conductive portion of the pin making contact with the guiding member, the device measures the penetrating depth and provides an indication thereof.

BRIEF DESCRIPTION OF THE DRAWINGS

The invention will now be described in connection with certain preferred embodiments with reference to the following illustrative figures, so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 illustrates the assembly for measuring the penetration depth of a dental instrument into a root canal of a tooth, according to the present invention;

FIG. 2 is an enlarged exploded view of the assembly of FIG. 1, according to the present invention;

FIG. 3 is a side view of the assembly as mounted on a tooth;

FIG. 4 illustrates stages of mounting the assembly on a tooth;

FIG. 5 is a perspective view of another embodiment of the present invention;

FIG. 6 is a perspective of still a further embodiment of the present invention;

FIGS. 7 and 8 are side views illustrating the steps in assembling the assembly shown in FIG. 6;

FIG. 9 is an exploded view of a modification of the present invention;

FIG. 10 is a perspective view of the assembly of FIG. 9;

FIG. 11 is an exploded view of a further modification of the present invention, and FIG. 12 is a perspective view of the embodiment of FIG. 11.

DETAILED DESCRIPTION OF PREFERRED EMBODIMENTS

The assembly 2 for measuring the penetration depth of a dental instrument into a tooth according to the present invention is illustrated in FIG. 1. Also illustrated is an electronic apex locator device 4 for continuously processing, displaying or otherwise indicating the depth of penetration of the dental instrument into the tooth during treatment. As seen, the device 4 is electrically connectable to the assembly, preferably by means of a plug 6 and socket 8 connection, however, the device 4 may just as well be directly plugged into a socket arranged at 10 (not shown), presently the connection point of the plug 6. Since the device 4 is per-se known, and does not constitute a part of the assembly 2 according to the present invention, no further detailed description is necessary.

Figure 2:
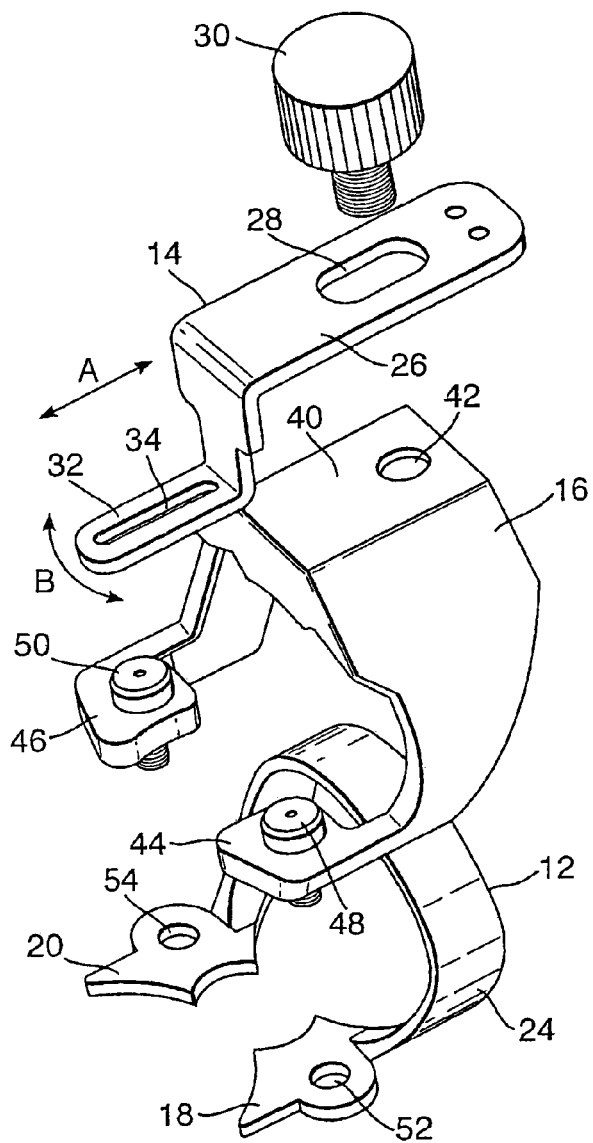
Figure 3:
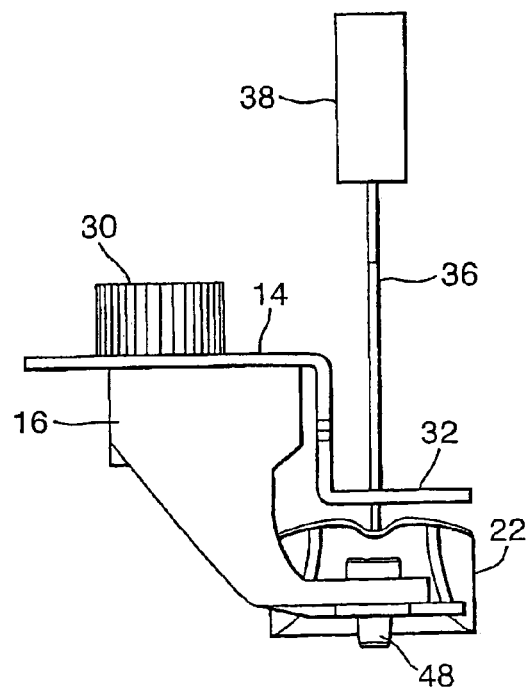

Referring now also to FIGS. 2 and 3 showing the preferred embodiment of assembly 2 in detail, it should be pointed out that while the Figures illustrate three major components of which the assembly 2 is composed, in fact the invention can be realized with two components only, namely, with a base element 12 and an electrically conductive guiding member 14. The third optional bracket 16 conveniently serves two purposes: clamping the guiding member 14 to the base 12, and insulating the metallic guiding member 14 from the base 12 which, due to considerations of strength, is usually made of metal.

The base 12 is configured in the form of an Ω, the two legs 18, 20 of which are adapted to be fastened on two opposite sides of a tooth 22, while the plane of the arched portion 24 is laterally displaced from the legs 18, 20, so as not to obscure the upper surface of the tooth 22.

The guiding member 14 has two interconnected portions, a first portion 26 made with an aperture 28 facilitating its connection, at least indirectly, to the base element 12, by means of a screw 30. The plane of the second portion 32 is vertically offset from the plane of the first portion 26, so as to extend in close proximity to the upper surface of the tooth 22, when assembled. The portion 32 has an opening 34 e.g., in the form of a hole or a slot, the diameter or the width of which is such as to allow the shaft 36 of a standard dental instrument 38, e.g., a drilling or filing instrument, to pass therethrough with clearance.

The bracket 16, made of an insulating material, is advantageously, similarly Ω-shaped, the two opposite sides of which are configured to straddle the flanks of the arched portion 24 of the base element 12 while a flat roof portion 40 abuts against the top section of the arch. If the bracket 16 is used, the guiding member 14 is screwed or otherwise coupled to the bracket by means of the threaded hole 42. The flanges 44, 46 of the bracket 16 are furnished with pegs 48, 50, configured to be pressure-fit into holes 52, 54 of legs 18, 20, so as to fixedly tighten the bracket 16 onto the base element 12.

It can now be understood that instead of the bracket 16, the guiding member 14 may be insulated at the portion where it makes contact with the metallic base element 12, and thus, the guiding member 14 may be directly coupled onto the base element 12, without short-circuiting. Obviously, guiding member 14 may, similarly, be made with insulated side sections providing better support thereof on the base element 12.

A preferred method of utilizing the assembly 2 will now be described with reference to FIG. 4. First, the base element 12 is clamped around the tooth 22 with the aid of a suitable tool, the edges of which are advantageously inserted in holes 52, 54 made in the legs 18, 20 for this purpose. After the base element 12 is clamped around the tooth 22, the guiding member 14 is screwed onto the bracket 16 and the combined unit is pressure fitted over the base element 12. The aperture 28 allows fine adjustment of the guiding member 14 above the tooth 22 in the direction of arrow A, as well as allows its swivelling, as indicated by arrow B, so as to align the slot above the required drilling and filing point in the tooth. The plug 6 is inserted in socket 8 and the assembly 2 in position, is now ready to accommodate the shaft 36 of the dental instrument 38.

Upon drilling or filing, the shaft 36 continuously or intermittently contacts the side walls of the opening 34, thereby closing an electrical circuit in the apex locator device 4 and activating same. It operates on the principle of impedance measurements between two electrodes, the first electrode constituted by the point on the shaft 36 of the instrument 38, making contact with the opening 34 of the guiding member 14, and the second electrode constituted by the electrode 56 (FIG. 1), which measurements differ depending on the frequencies. The device 4 monitors the changes in impedances, as the shaft 36 of the instrument 38 approaches the apex. The measurements performed and indicated by the apex locator device 4 are actually per-se known, e.g., from International Patent Application No. PCT/IL02/00556.

Figure 5:
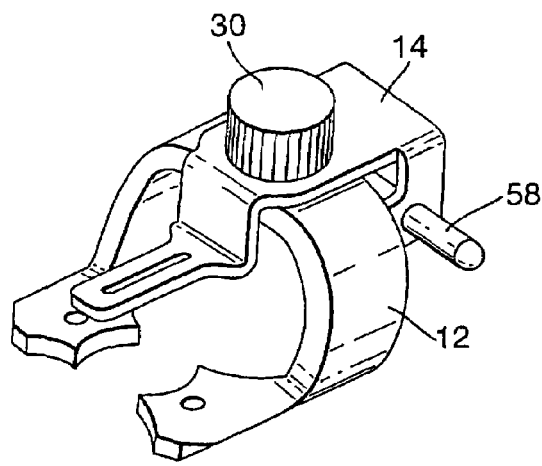

FIG. 5 illustrates another embodiment according to the present invention showing a base element 12 made of electrical insulating material, e.g., plastic, or alternatively, is plastic coated, and a guiding member 14 directly attachable thereon by means of the screw 30. Also seen is a plug 58 for electrically connecting to a suitable socket 8 of an apex locator device 4 (not shown).

Figure 6:
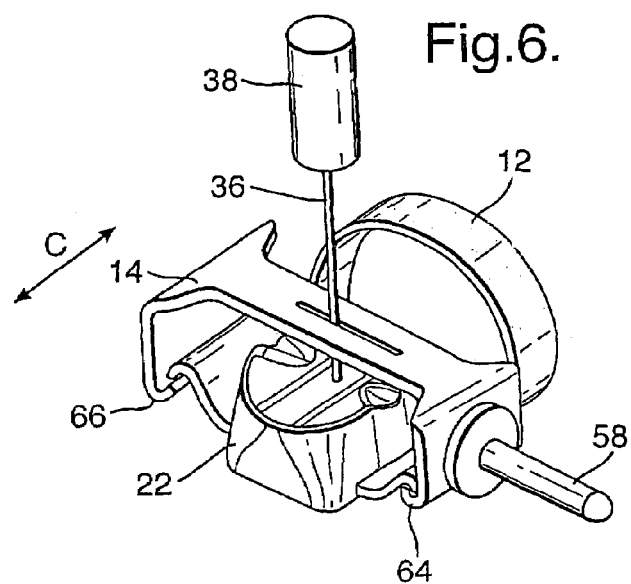
Figure 7:
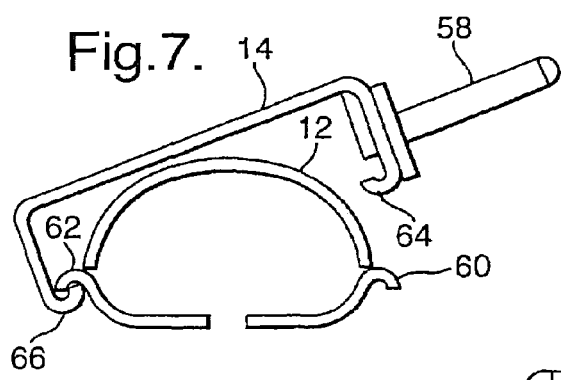
Figure 8:
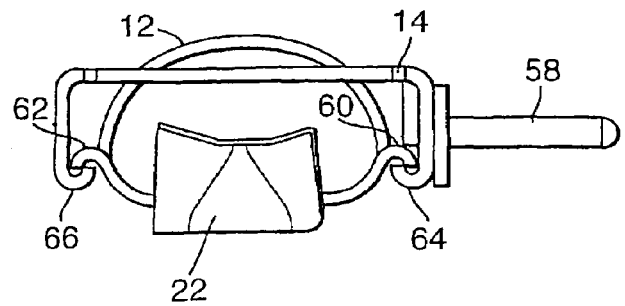

A slight modification of the embodiment of FIG. 5 is shown in FIGS. 6 to 8. Accordingly, the base element 12 is formed with flexible ledges 60, 62 and the bridge-like conductive guiding member 14 is formed with inwardly curved lips 64, 66, configured to substantially match the curvature of the ledges 60, 62. The inter-connection between the base element 12 and guiding member 14 is thus effected in two stages, as illustrated in FIGS. 7 and 8. First, the lip on one side of the guiding member 14 is hooked into one ledge, say lip 66 into ledge 62, and thereafter, the other lip 64 is pressed into place in ledge 60. The conductive element 14 can be moved in the direction of Arrow C during use. While guiding member 14 of FIGS. 1 to 5 is oriented across the base element 12, the guiding member 14 of FIGS. 6 to 8 extends parallel thereto. In both cases, however, the opening 34 in guiding member 14 is located above the tooth 22 and is not obscured by the base element 12.

Figure 9:
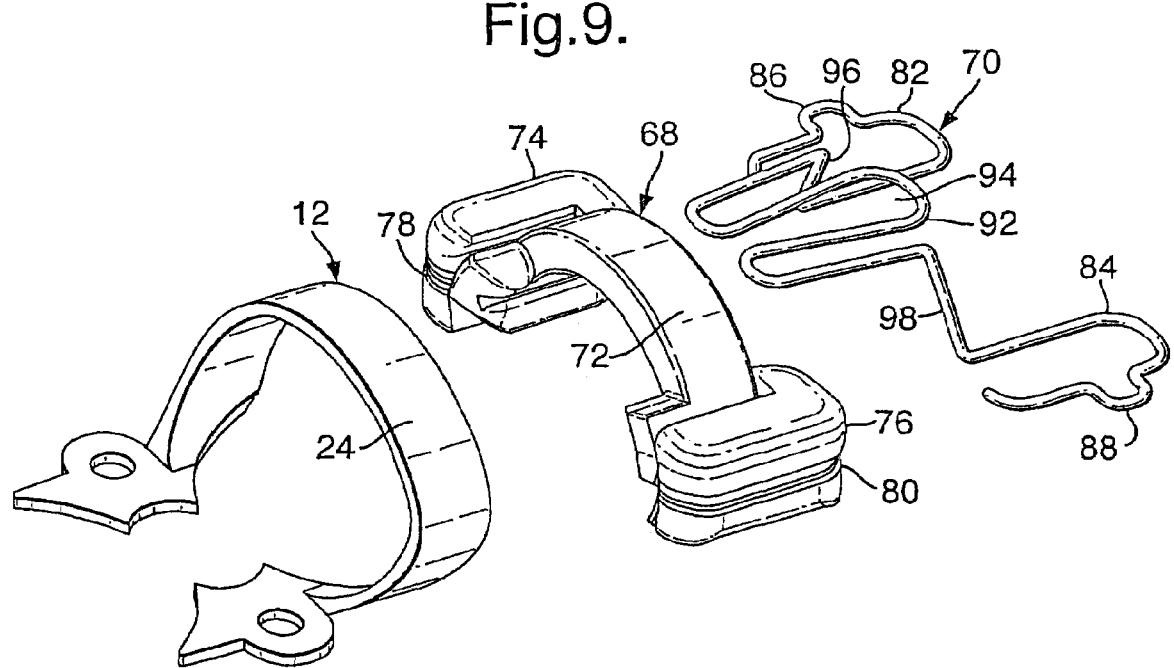
Figure 10:
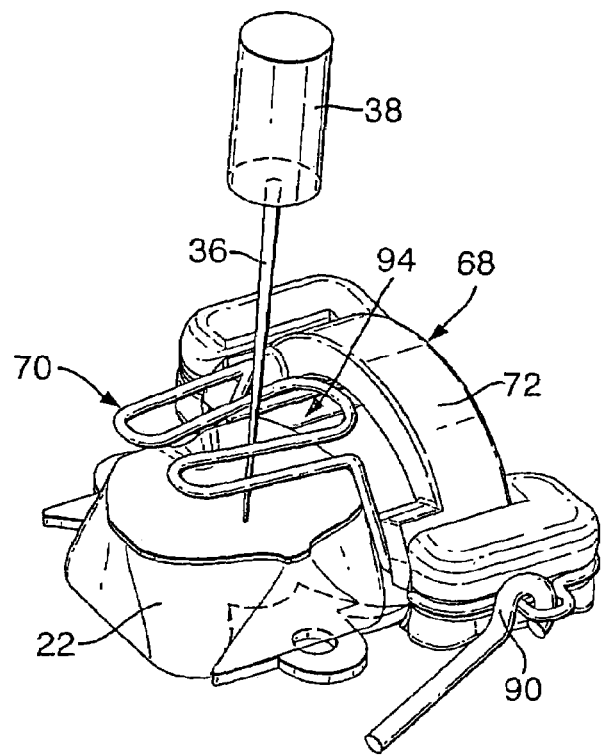

A further modification is illustrated in FIGS. 9 and 10. This assembly of this embodiment, similar to the embodiment of FIG. 2, is composed of three parts: the standard base element 12, an electrically non-conductive bracket 68 and an resilient electrically conductive guiding member 70, advantageously made of a bent electrical wire. The bracket 68 is composed of an arched portion 72 and two side shoulders 74, 76 and is configured to be press-fitted onto the base element 12, so as to straddle at least the arched portion 24 thereof and be fixedly retained by it. The shoulders 74, 76 of the bracket 68 are provided, on their lateral outside surfaces, with recesses 78, 80, for retaining outside loops 82, 84 of the resilient conductive guiding member 70. The loops 82, 84 are made with lugs 86, 88, serving as sockets into which a hook-shaped electrical conductor 90, leading to an electronic apex locator device 4 (FIG. 1), can be inserted. As seen in the drawings, the intermediate portion 92 of the guiding member 70, made of a meandering piece of wire, defines an opening 94 through which the shaft 36 of a dental instrument 38 can pass and contact the wire defining the opening 94. The intermediate portion 92, disposed at a higher level than the level of loops 82, 84 and the loops 82, 84 are interconnected by pieces of wire 96, 98.

Figure 12:
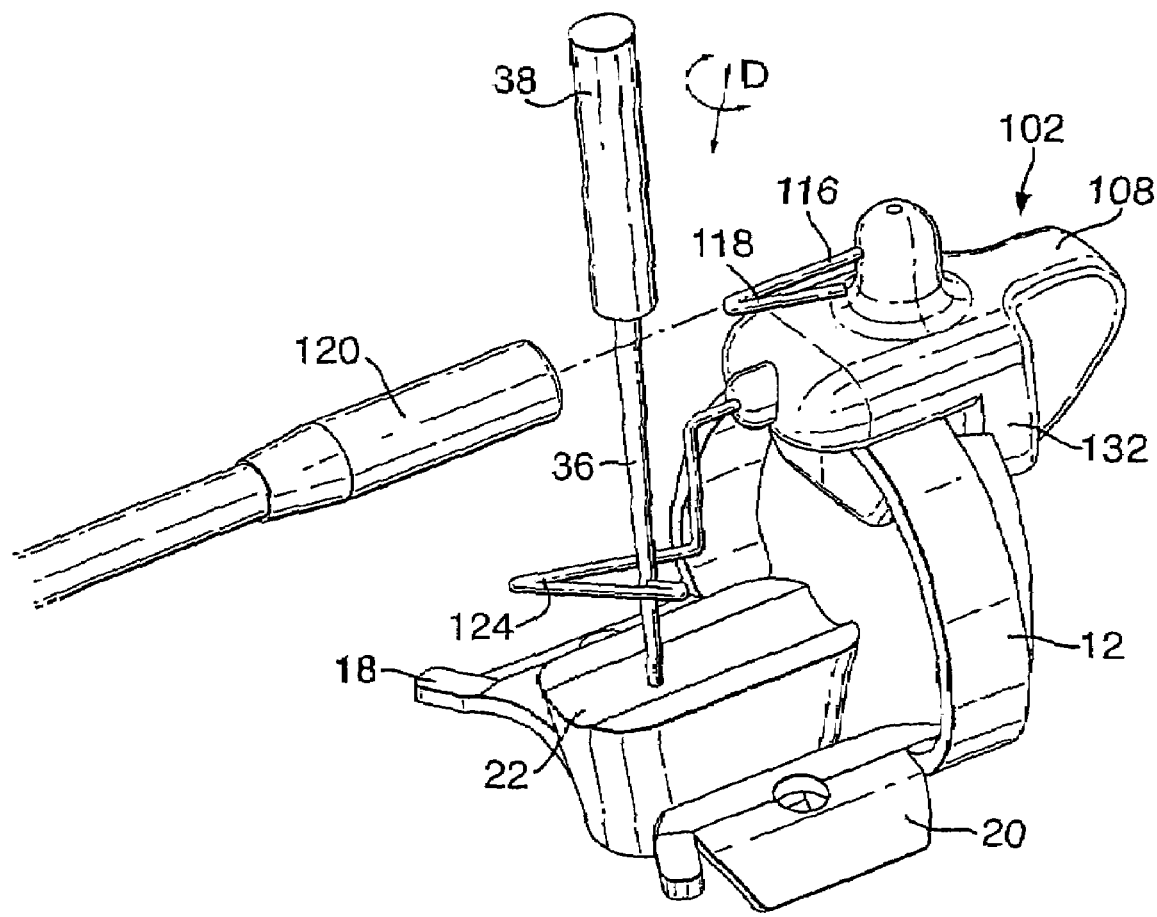

Still a further modification of the present invention is illustrated in FIGS. 11 and 12. This modification is similar to that of FIGS. 9 and 10 in that it utilizes an electrically conductive guiding member 100, constituted by a bent metal wire. The assembly is composed of three parts: a base element 12, an electrically non-conductive bracket 102 and the resilient conductive guiding member 100. The bracket 102 is U-shaped, having two parallelly extending legs 104, 106 and a web portion 108. The legs 104, 106 define between themselves a slot 110 sized to accommodate the arched portion 24 of the base element 12. The upper leg 104 has a through-going hole commencing at its front edge 112 and terminating at its top surface at 114. The size of the hole is calculated to be substantially the same as the diameter of the conductive guiding member 100. As seen in FIG. 11, the conductive guiding member 100 has three major portions: a first portion 116, in assembly, protruding from the upper leg 104 through the hole at 114, the portion advantageously being provided with a bent edge 118 for connection with a socket 120, leading to an electronic apex locator device 4 (see FIG. 1); a second portion 122 being configured to extend inside the leg 104 and exit the front edge 112, and a third portion 124 extending above a tooth 22 clamped between legs 18, 20 of the base element 12. Portion 124 may also be vertically offset from portion 122, in the direction of tooth 22, by a connecting part 126 and may also be provided with a bent extension 128.

As can be understood and seen in the Figures, the non-conductive bracket 102 is preferably produced e.g., by molding together with the guiding member 100. The bracket 102, together with the guiding member 100 is slid under pressure onto the arched portion 24 of the base element 12. In order to assure that the bracket 102, will stay in place during use, the arched portion 24 may be provided with a cutout 130, having a width substantially the same as the width of the web portion 108 of the bracket 102 for abutting against opposite sides 132 of the web portion 108, as can be seen in FIG. 12. The portion 116 of the member 100 is resilient, and thus, it can be angularly swung, as indicated by the arrows D in all directions and any convenient angle, and retained in this position, as conveniently disposed by the user. During use, the shaft 36 of the dental instrument 38 makes electrical contact with the portion 124 of the member 100, conducting the electrical signals from and to the electronic device 4, e.g., an apex location measuring device.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An assembly for measuring the penetration depth of a dental instrument into a root canal of a tooth, said assembly comprising:
    a base element for bracing onto a tooth to be treated, said base element being substantially omega-shaped having two legs and an arch extending along a plane laterally displaced from the legs;
    an electrically non-conductive U-shaped bracket having two parallel extending legs and a web portion therebetween configured to be coupled to the arch of said base element; and
    an electrically conductive guiding member affixable to said bracket and disposed, when assembled, above a tooth clamped between the legs of said base element, said guiding member having a first portion with an electrical terminal for electrically connecting with a socket of an apex location measuring device, a second portion extending in one of said legs of the bracket and a third portion extending above said tooth clamped by said base element,
    whereby, in use, a portion of said dental instrument makes electrical contact with said guiding member to measure the penetration depth of the dental instrument into the root canal of the tooth.

2. The assembly as claimed in claim 1, wherein said electrically conductive guiding member is made of a bent wire.

3. The assembly as claimed in claim 2, wherein said bent wire includes a straight portion.

4. The assembly as claimed in claim 1, wherein the first portion of said guiding member is provided with a bent edge for making an electrical contact with said socket.

5. The assembly as claimed in claim 4, wherein said bent edge is resilient, facilitating bending in a plurality of directions.

6. The assembly as claimed in claim 1, wherein the base element has an arched portion made with a cutout and the width of said web portion is sized to fit in said cutout.

* * * * *